(12) United States Patent
Sheabar et al.

(10) Patent No.: US 7,371,418 B2
(45) Date of Patent: *May 13, 2008

(54) METHOD FOR CONTROLLING THE YIELD AND PURITY OF PROTEINASE INHIBITOR II DURING EXTRACTION

(76) Inventors: Fayad Z. Sheabar, 5691 Vista Dr., West Des Moines, IA (US) 50266; Robert Stomp, 4032 E. Hubbell #292, Des Moines, IA (US) 50317

(*) Notice: Subject to any disclaimer, the term of this patent is extended or adjusted under 35 U.S.C. 154(b) by 2 days.

This patent is subject to a terminal disclaimer.

(21) Appl. No.: 09/900,057

(22) Filed: Jul. 6, 2001

(65) Prior Publication Data

US 2003/0092150 A1 May 15, 2003
US 2005/0037474 A9 Feb. 17, 2005

Related U.S. Application Data

(63) Continuation-in-part of application No. 09/900,555, filed on Jul. 6, 2001, now Pat. No. 6,767,566.

(51) Int. Cl.
*A61K 36/81* (2006.01)
*A61K 36/00* (2006.01)

(52) U.S. Cl. .................. 424/773; 424/725; 514/2; 514/783; 426/425

(58) Field of Classification Search ............. 424/195.1, 424/725; 435/219; 210/634; 426/425
See application file for complete search history.

(56) References Cited

U.S. PATENT DOCUMENTS

| 4,491,578 A | 1/1985 | Peikin |
| 4,906,457 A | 3/1990 | Ryan |
| 5,187,154 A | 2/1993 | Phillips et al. |

FOREIGN PATENT DOCUMENTS

| EP | 0487480 A2 * | 5/1992 |
| WO | WO 99/01474 * | 1/1999 |
| WO | WO-9901474 | 1/1999 |

OTHER PUBLICATIONS

Melville, J.C. and Ryan, C.A., "Chymotrypsin inhibitor I from potatoes", *J. Biological Chem.*, 1972, 247: p. 3445-3453.
Ryan, C.A., "Purification and properties of a carboxypeptidase inhibitor from potatoes", *J. Biological Chem.*, 1974, 249: p. 5495-5499.
Bryant, J., Green, T.R., Gurusaddaiaht, T., and Ryan, C.A., "Proteinase inhibitor II from potatoes: Isolation and characterization of its protomer components", *Biochemistry*, 1976, 15: p. 3418-3424.
Huang, C., MA, W.Y., Ryan, C.A., and Dong, Z., "Proteinase inhibitors I and II from potatoes specifically block UV-induced activator protein-1 activation through a pathway that is independent of extracellular signal regulated kinases, c-jun N-terminal kinases, and P38 kinase", *Proc. Natl. Acad. Sci.*, 1997, 94:11957-11962, US.

Schwartz, J.G., Guan, D., Green, G.M., and Phillips, W.T., "Treatment with an oral proteinase inhibitor slows gastric emptying and actually reduces glucose and insulin levels after a liquid meal in type II diabetic patients", *Diabetes Care*, 1994, 17: p. 255-262.
Hill, A.J., Peikin, S.R., Ryan, C.A., and Blundell, J.E., "Oral administration of proteinase inhibitor II from potatoes reduces energy intake in man", *Physiol. Behav.*, 1990, 48: p. 241-246.
Pearce, G. and Ryan, C.A., "A rapid, large-scale method for purification of metallo-carboxypeptidase from potato tubers", *Anal. Biochem.*, 1983, 30: p. 223-225.
Walsh, T.A. and Twitchell, W.P., "Two Kunitz-type proteinase inhibitors from potato tubers", *Plant physiology*, Sep. 1991, v. 97 (1): p. 15-18.
Greenblatt, H.M., Ryan, C.A., and James, M.N.G., "Structure of the complex of *Streptomyces griseus* proteinase B and polypeptide chymotrypsin inhibitor-1 from Russet Burbank potato tubers at 2.1 angstrom resolution", *Journal of molecular biology*, Jan. 5, 1989, v. 205 (1): p. 201-228.
Wang, K.E. and Zhong, J.L., "The isolation and immmunological properties of potato proteinase II", *Acta Biochimica et Biophysica Sinica*, 1992, v. 24 (2): p. 189-192, English Abstract.
Uchida, K., Iwasaki, T., Kiyohara, T., and Yoshikawa, M., "Isolation and characterization of polypeptide inhibitors from potato tubers", *Science Reports of Faculty of Agriculture*, 1983, 15 (2): p. 357-365, Kobe University.
Kaiser, K.-P. and Santarius, K., "Thermo stable basic proteinase inhibitors from potatoes. Isolation and characterization", Zeitschrift fur Lebensmittel-Untersuchung und-Forschung, 1977, English Abstract.
Santarius, K. and Belitz, H.-D., "Proteinase inhibitors. V. Isolation and some properties of A 5 inhibitor from potatoes", Chemie Mikrobiologie Technologie der Lebensmittel, Y1 (Jan. 1972), p. 56-62, Inst. Fur Lebensmittelchemie, Tech. Univ., Munich, English Abstract.
Kaiser, K.-P. and Belitz, H.-D., Chemie Mikrobiologie Technologie der Lebensmittel 1971, 1: 1-7, Inst. Fur Lebensmittelchemie, Tech. Univ., Munich, English Abstract.

* cited by examiner

*Primary Examiner*—Patricia Leith
(74) *Attorney, Agent, or Firm*—Kent A. Herink; Emily E. Harris

(57) ABSTRACT

The present invention provides a method for adjusting the yield and purity of a proteinase inhibitor extract from plant tissue, preferably potato tubers. The extraction and isolation of the proteinase inhibitor from potatoes begins with the addition of an organic acid, preferably formic acid, and a salt, preferably sodium chloride, to raw potatoes. The mixture is subjected to process steps to extract soluble proteins. The extract is subjected to heat treatment at an adjusted temperature and adjusted duration whereby purity of the proteinase inhibitor is enhanced by heating at a relatively high temperature for a relatively short duration and whereby yield of the proteinase inhibitor is enhanced by heating at a relatively low temperature for a relatively long duration. If the removal of soluble protein impurities that are not denatured during the heat treatment step is desired, ultrafiltration is used. By adjusting the cycles of filtration, purity of the proteinase inhibitor can be adjustably selected.

11 Claims, No Drawings

METHOD FOR CONTROLLING THE YIELD AND PURITY OF PROTEINASE INHIBITOR II DURING EXTRACTION

This application is a continuation-in-part of U.S. application Ser. No. 09/900,555, filed Jul. 6, 2001 now U.S. Pat. No. 6,767,566.

BACKGROUND OF THE INVENTION

1. Field of the Invention

The present invention relates to the isolation and purification of a proteinase inhibitor, and more specifically, to a method for controlling the yield and purity of Proteinase Inhibitor-II (PI2) extracted from whole potatoes by adjusting heat treatment and filtration conditions.

2. Background of the Prior Art

Proteins that inhibit proteolytic enzymes are often found in high concentrations in many seeds and other plant storage organs. Inhibitor proteins are also found in virtually all animal tissues and fluids. These proteins have been the object of considerable research for many years because of their ability to complex with and inhibit proteolytic enzymes from animals and microorganisms. The inhibitors have become valuable tools for the study of proteolysis in medicine and biology. Protease inhibitors are of particular interest due to their therapeutic potentials in controlling proteinases involved in a number of disorders such as pancreatitis, shock, and emphysema, and as agents for the regulation of mammalian fertilization. Potato tubers are a rich source of a complex group of proteins and polypeptides that potently inhibit several proteolytic enzymes usually found in animals and microorganisms. In particular, potato inhibitors are known to inhibit human digestive proteinases, and thus have application in the control of obesity and diabetes.

Two broad classes of protease inhibitor superfamilies have been identified from soybean and other legumes with each class having several isoinhibitors. Kunitz-type inhibitor is the major member of the first class whose members have 170-200 amino acids, molecular weights between 20,000 and 25,000, and act principally against trypsin. Kunitz-type proteinase inhibitors are mostly single chain polypeptides with 4 cysteines linked in two disulfide bridges, and with one reactive site located in a loop defined by disulfide bridge. Kunitz inhibitor is capable of inhibiting trypsin derived from a number of animal species as well as bovine chemotrypsin, human plasmin, and plasma kallikrein. The cationic form of human trypsin, which accounts for a majority of trypsin activity, is only weakly inhibited by the Kunitz inhibitor, whereas the anionic form is fully inhibited.

The second class of inhibitors contains 60-85 amino acids, has a range in molecular weight of 6000-10,000, has high proportion of disulfide bonds, is relatively heat-stable, and inhibits both trypsin and chemotrypsin at independent binding sites. Bowman-Birk inhibitor is an example of this class. The Bowman-Birk inhibitor is a 71 amino acid chain protein with 7 disulfide bonds characterized by its low molecular weight of about 8000 (in non-associated monomers), high concentration (about 20%) of cystine, high solubility, resistance to heat denaturation and having the capacity to inhibit trypsin and chemotrypsin at independent inhibitory sites.

Proteinase inhibitors extracted from potatoes have been distinguished into two groups based on their heat stability. The group of inhibitors that is stable at 80° C. for 10 minutes have been identified as inhibitor I (mol. wt. 39,000) (Melville, J. C. and Ryan, C. A. Chymotrypsin inhibitor I from potatoes. *J. Biological Chem.*, 247: 3445-3453, 1972), carboxypeptidase inhibitor (CPI) (mol. wt. 4,100) (Ryan, C. L., Purification and properties of a carboxypeptidase inhibitor from potatoes. *J. Biol. Chem.* 249: 5495-5499, 1974), inhibitors IIa and IIb (mol. wt. 20,700) (Bryant, J., Green, T. R., Gurusaddaiah, T., Ryan, C. L. Proteinase inhibitor II from potatoes: Isolation and characterization of its protomer components. *Biochemistry* 15: 3418-3424, 1976), and inhibitor A5 (mol. wt. 26,000).

In 1972, Melville and Ryan (Melville et al.) reported a large-scale preparation for isolating Chymotrypsin Inhibitor I from potato tubers. According to the method of Melville and Ryan, potatoes were sliced with peels intact and soaked in a sodium dithionite solution, homogenized, and expressed through nylon cloth. The resulting juice was adjusted to a pH of 3, centrifuged at 1000×g for 15 minutes at 5° F., and the supernatant collected and fractionated with ammonium sulfate.

Purification was achieved through water washing and heat treatment whereby clear filtrates of heated fractions were pooled and lyophilized. Suspending the lyophilized powder in water, dialyzing it against water for 48 hours, and lyophilizing the resulting clear filtrate obtained a crude extract. Resuspended extract was then centrifuged and applied to a column of Sephadex G-75. Collected fractions containing the Inhibitor I were pooled, evaporated, and desalted on a column of Sephadex G-25. The resulting gel-filtered inhibitor product was determined to be approximately 90% Inhibitor I protein purified by dissociation on a Sephadex G-75 column and desalted on a column of Sephadex G-25.

The Ryan lab followed-up by reporting the isolation and characterization of Proteinase Inhibitor II in much the same manner as described for Inhibitor I (Bryant, J., Green, T. R., Gurusaddaiah, T., Ryan, C. L. Proteinase inhibitor II from potatoes: Isolation and characterization of its protomer components. *Biochemistry* 15: 3418-3424, 1976). Bryant et al. differentiated potato-derived proteinase inhibitors into two groups based on their respective stabilities to a temperature of 80° C. for 10 minutes. Proteinase Inhibitor I (PI1) is characterized as a tetrameric protein composed of four hybridized isoinhibitor protomer species having a molecular weight of 39,000, whereas PI2 is characterized as a dimeric inhibitor comprising four isoinhibitor promoter species having a molecular weight of 21,000.

The isolation of proteinase inhibitor proteins from potatoes is described in WO 99/01474. Proteins from potato tubers are extracted in soluble form in an aqueous/alcohol extraction medium, such as dilute formic acid and 20% ethanol. The alcohol extract is heated to a first temperature to denature most of the unwanted proteins and cooled to a second temperature to form a precipitate phase constituting the debris and a soluble phase that contains the heat stable proteinase inhibitor proteins. The heat stable proteinase inhibitor proteins are precipitated from the soluble phase by dialysis against a suitable dialysis medium, such as dilute formic acid.

U.S. Pat. No. 5,187,154 describes a method for the diagnosis and the treatment of individuals with diabetes or at risk to develop diabetes mellitus. In particular, gastric emptying determinations are used to assess risk. Risk or early symptoms associated with subsequent development of diabetes mellitus may be controlled or alleviated by delaying gastric emptying, which was achieved by the administration of cholecystokinin.

U.S. Pat. No. 4,906,457 describes compositions and methods for reducing the risk of skin cancer. The described compositions included at least one effective protease inhibitor. Preferred protease inhibitors included serine protease inhibitors and metallo-protease inhibitors. The protease inhibitors were preferably included in concentrations ranging from approximately 10 picograms to 10 milligrams per milliliter of the skin-applicable topical mixtures. The topical mixtures preferably included a suitable topical vehicle such as a cream, lotion, or ointment. One class of anti-carcinogenic skin treatment compositions of this invention preferably included the desired protease inhibitors in combination with a suitable sunscreen agent or agents, such as para-amino benzoic acid, to provide particularly advantageous compositions for reducing the risk of sunlight-induced skin cancer.

When applied to mouse epidermal JB6 cells, proteinase inhibitors I and II from potatoes blocked the UV induced transcription factor activator protein-1 (AP-1), which has been shown to be responsible for the tumor promoter action of UV light in mammalian cells. The inhibition appears to be specific for UV induced signal transduction for AP-1 activation. Furthermore, the inhibition of UV induced AP-1 activity occurs through a pathway that is independent of extracellular signal-regulated kinases and c-jun N-terminal kinases as well as P38 kinases (Huang, C., Ma, W. Y., Ryan, C. A., Dong, Z. Proteinase inhibitors I and II from potatoes specifically block UV-induced activator protein-I activation through a pathway that is independent of extracellular signal regulated kinases, c-jun N-terminal kinases, and P38 kinase. *Proc. Natl. Acad. Sci., US,* 94: 11957-11962, 1997).

U.S. Pat. No. 4,491,578 describes a method of eliciting satiety in mammals through the administration of an effective amount of a trypsin inhibitor. The method was based on the postulate that the enzyme trypsin, normally secreted by the pancreas, constitutes a negative feedback signal for cholecystokinin secretion that in turn comprises a putative satiety signal. Thus, the effect of the trypsin inhibitor is to increase the concentration of cholecystokinin secretion advancing the sensation of satiety resulting in a consequent decrease in food intake and, over time, body weight.

The effect of PI2 extracted from potatoes, which increases CCK release, on food intake was examined in 11 lean subjects. Five minutes before presenting them with a lunchtime test meal, volunteers received 1.5 g PI2 in a high protein soup vehicle (70 kcal), the soup vehicle alone, or a no-soup control, according to a double blind, within subject design. The consumption of the soup alone led to a non-significant 3% reduction in energy intake. The addition of 1.5 g PI2 to the soup significantly reduced energy intake by additional 17.5%. Pre-meal ratings of motivation to eat and food preferences did not predict the reduction in energy intake by the proteinase inhibitor. Based on the results, the authors concluded that endogenous CCK may have an important role in the control of food intake and that proteinase inhibition may have a potential for reducing food intake (Hill et al., 1990).

The efficiency of oral ingestion of trypsin/chemotrypsin inhibitor in delaying the rate of gastric emptying in recently diagnosed type II diabetic patients and improving their post-prandial metabolic parameters have been examined (Schwartz, J. G., Guan, D., Green, G. M., Phillips, W. T.). Treatment with an oral proteinase inhibitor slows gastric emptying and actually reduces glucose and insulin levels after a liquid meal in type II diabetic patients. *Diabetes Care,* 17: 255-262, 1994). Serum insulin, plasma glucose, plasma gastric inhibitory polypeptide levels, and the rate of gastric emptying were all significantly decreased over the 2 hour testing period in subjects who received proteinase inhibitor in their oral glucose/protein meal. U.S. Pat. No. 5,187,154 suggests that the administration of CCK can be made through an intramuscular injection or an intranasal spray. Alternatively, an oral administration of an agent that enhances endogenous release of CCK could represent an important approach to the treatment of Type 2 diabetes. One of the agents that may have a therapeutic application in patients with recently diagnosed Type 2 diabetes can be the potato proteinase inhibitor II.

Recently, PI2 has been implicated in playing a role in extending satiety in subjects fed a nutritional drink composition containing PI2. U.S. patent application Ser. No. 09/624,922 describes that subjects reported a significant reduction in hunger for up to 3½ hours post meal when fed a meal comprising a nutritional drink composition containing PI2. Likewise, fullness ratings were enhanced, and each study subject lost an average of 2 kg over a 30-day period without experiencing the adverse side effects typically associated with appetite suppressing compounds. Mechanistically, it is thought that as a trypsin and chymotrypsin inhibitor, when consumed by a subject, PI2 stimulates the release of endogenous cholecystokinin, a known putative feedback agent effective in reducing the desire to intake food.

Proteinase inhibitor II is seen to have potential applicability in a number of areas affecting human health. In addition, PI2 may be administered in a variety of ways, including orally, intramuscularly, intranasally, and topically, and will be provided in a variety of carriers and diluents. In certain applications, for example in the control of satiety, it has been found that a relatively pure form of PI2 is needed and that the presence of impurities, such as Kunitz inhibitors, adversely affects the efficacy of the PI2. In other applications, purity will likely not be as critical so that the extraction process could be simplified, thereby reducing the cost of the PI2 product. Accordingly, a need exists for a large-scale isolation and purification process to extract PI2 in a cost-effective and efficient manner meeting commercial qualitative and quantitative standards.

A technique capable of large-scale isolation and purification is ultrafiltration, a type of membrane filtration and separation technique that utilizes membranes having pore sizes between 0.001 and 0.1 µm. Methodologies utilizing ultrafiltration are particularly useful for concentrating dissolved molecules such as proteins, peptides, nucleic acids, carbohydrates, and other biomolecules, as well as desalting, exchanging buffer, and gross fractionation. Diafiltration is a selective fractionation process of washing smaller molecules through a membrane, while leaving the larger molecule of interest in the retained solution, also known as retentate. In selecting a membrane suitable for filtering a target molecule, the molecular weight cutoff (MWCO) of a membrane is utilized to define the ability of the membrane to exclude molecules on a size basis. 90% of an ideally globular molecule. MWCO is the size designation (in kilodaltons "KD") for ultrafiltration membranes. The term Nominal Molecular Weight Cutoff (NMWCO) is defined as a membrane's ability to retain 90% of an ideally globular molecule having the designated molecular weight.

As discussed above, ultrafiltration is a technique used for the separation under elevated pressure of dissolved molecules in solution on the basis of size. Molecules larger than the pore size of the membrane will not pass through the membrane surface and will remain in the retentate, and may further be retained on the surface of the membrane. Accumulations of retained molecules on the membrane typically form a gel layer, significantly reducing the separation performance characteristics of the membrane. Separation capacity of a given ultrafiltration system is a function of the ability of the selected membrane to allow the smaller particles to pass through the membrane in the permeate, while minimizing gel formation in the retentate. However, a direct correlation between a molecular weight and size does not always exist.

Molecular conformations (including both intermolecular and intramolecular interactions) can significantly alter the apparent size of a molecule. Having numerous modes of interaction available, proteins are particularly susceptible to conformational changes while dissolved in solution. Solution characteristics such as pH, solute concentration, temperature, and ionic strength significantly affect the apparent size of particles and molecules in solution, and therefore affect conformational characteristics as well.

SUMMARY OF THE INVENTION

The invention consists of a process that utilizes heat treatment of potato proteins in the presence of salt, followed by centrifugation and filtration, as an efficient method for the elimination of Kunitz family, Bowman-Birk proteinase and carboxypeptidase inhibitors from other potato proteinase inhibitors. Raw potatoes are mixed with an organic acid, preferably formic acid, and a salt, preferably sodium chloride. The mixture is comminuted to reduce the size and increase the surface area of potato particles. The soluble proteins, including PI1, PI2, Kunitz family, Bowman-Birk and carboxypeptidase inhibitors, are released into the liquid phase and the mixture is centrifuged to remove solids.

The supernatant is incubated at a temperature of between about 60° C. and about 90° C., for between about 30 minutes and about 180, minutes, to denature the impurity proteins without denaturing PI2. The temperature and time of incubation are selected to adjust the purity and yield of the PI2.

Centrifugation is used to remove the denatured impurity proteins from the heat-treated supernatant. Ultrafiltration using a cellulosic or sepharose membrane combined with diafiltration is used to remove the carboxypeptidase inhibitor.

The heat treatment stage of the process of the present invention can be adjusted to be highly efficient in the separation and removal of Kunitz type inhibitor, previously found to interfere with the satiety efficacy of the PI2 in humans. The filtration stage of the present process also can be adjusted to be highly efficient in the separation and removal of Bowman-Birk and carboxypeptidase inhibitors and to provide high recovery and yield of the PI2 inhibitor, increasing the concentration of PI2 in the final product by more than 100 times in comparison to its concentration in the proteins fraction in the raw potatoes. The process is efficient at laboratory, pilot plant and production scales, is easy to perform and does not require specialized equipment.

An object of the present invention is to provide a method for separating and removing soluble protein impurities from extracts of plant materials.

Another object of the present invention is to provide a method for providing a high yield of PI2 for extracts of PI2-containing plant materials.

A further object of the present invention is to provide a method whereby the purity and yield of PI2 from plant materials may be selectively or jointly controlled

DETAILED DESCRIPTION OF THE INVENTION

The extraction and isolation of PI2 from potatoes begins with the addition of an organic acid, preferably formic acid, and a salt, preferably sodium chloride, to raw potatoes. The mixture is subjected to comminution to reduce the particle size of the potato particles and extract soluble proteins. Centrifugation is used to remove solids and the liquid fraction is heated at a temperature sufficient to denature many undesired proteins but not PI2. The solution is again centrifuged to remove the insoluble denatured proteins and the liquid fraction is microfiltered to remove relatively large particles. Ultrafiltration is used to further purify the PI2 in the retentate. The retentate is dried, for example by lyophilization, to result in a powdered product.

Reverse Phase HPLC Method

The amount of PI2, Kunitz and carboxypeptidase inhibitors was measured using reverse phase HPLC. A Microsorb C-18 column (4.6 mm×250 mm, 5 µm particles with 300 Angstrom pore size; Varian Analytical Instruments) was used. Two mobile phase solvents were prepared, solvent A was 800 g deionized $H_2O$, 150 g acetonitrile, and 0.95 trifluoroacetic acid, and solvent B was 850 g acetonitrile and 0.85 g trifluoroacetic acid. Approximately 50 mg of the sample was added to 100 ml of solvent A. The sample was vortexed for 30 seconds, and then centrifuged at 10,000 rpm for 10 minutes. The supernatant was collected for RP-HPLC analysis. One hundred µl of the sample was injected into the column, with the pump set at 800-2500 psig, and a temperature of 30.0° C. The other flow rate, time, and solvent compositions are as set out in Table 1. The diode array of the detector was set at 220 nm.

TABLE 1

| HPLC Conditions | | |
|---|---|---|
| Time (min) | Flow rate (ml/min) | Solvent Composition (volume %) |
| 0 | 1 | 100% A |
| 5 | 1 | 100% A |
| 34 | 1 | 38% A |
| 38 | 1 | 100% B |
| 40 | 2 | 100% B |
| 45 | 2 | 100% B |
| 50 | 1 | 100% A |
| 55 | 1 | 100% A |

An external standard was prepared to construct a standard curve for calibration of the column. Five mg of BSA were dissolved in 10 ml of solvent A. Four volumes, i.e., 25, 50, 75, and 100 µl, were injected into the column. A calibration curve was generated from the results.

Heat Treatment/Denaturation Stage

Experiment 1

The temperature required to denature and precipitate protein impurities was first examined. A lot of potatoes was extracted and filtered using an extractant consisting of 1.0 N sodium chloride and 1.5% formic acid. This extract was filtered and aliquoted for the heat-treatment study. Each sample of the extract was placed in a test tube, and then heated to the target temperature using a constant temperature water bath. Samples were taken at times 0 minutes, 15 minutes, 30 minutes, 45 minutes and 60 minutes. The samples were immersed in an ice bath and then centrifuged in an Eppendorf 5415 centrifuge for 5 minutes at 10,000×g to remove precipitated material. The supernatant was analyzed using the reverse phase HPLC method described above and the Kunitz peaks were quantified. The results are reported in Table 2.

TABLE 2

Kunitz Impurities Remaining in Solution

| Temperature ° C. | Time (minutes) | Kunitz[1] mg/ml |
|---|---|---|
| 70 | 0 | 0.819 |
| 70 | 15 | 0.158 |
| 70 | 30 | 0.128 |
| 70 | 45 | 0.119 |
| 70 | 60 | 0.110 |
| 80 | 0 | 0.874 |
| 80 | 15 | 0.131 |
| 80 | 30 | 0.105 |
| 80 | 45 | 0.101 |
| 80 | 60 | 0.095 |
| 90 | 0 | 0.878 |
| 90 | 15 | 0.112 |
| 90 | 30 | 0.108 |
| 90 | 45 | 0.100 |
| 90 | 60 | 0.099 |

[1]The value for the Kunitz impurity is the summation of all protein eluting after the carboxypeptidase doublet using the reverse phase-HPLC methodology described in detail below.

It is clear from the data that there is a time advantage to be gained, in terms of rapidity of impurity removal, by treating the product at a temperature of 90° C. After incubating for 15 minutes at 90° C. the removal of the Kunitz type proteins was equivalent to that of heating for 60 minutes at 70° C. or heating for 30 minutes at 80° C. Unfortunately, as PI2 has limited stability at 90° C., it is necessary to treat at a lower temperature to minimize PI2 degradation and loss. Removal of the Kunitz type proteins was efficiently accomplished by raising the product temperature to 70° C. for 60 minutes. Heating the extract to 70° C. for 15 minutes generated an 81% reduction in the amount of Kunitz proteins and after 60 minutes at 70° C. this reduction had reached of 87%.

A further trial was run to determine the effect of heat treatment at various temperatures and time periods on the amount of PI2, carboxypeptidase inhibitor (CPI), Kunitz type proteins and overall purity. The conditions and results are as reported in Table 3.

TABLE 3

Protein purities of PI2 preps incubated at 60° C. through 80° C.

| Sample | PI2 (mg/ml) | CPI (mg/ml) | Kunitz (mg/ml) | Overall purity | PI2/Kunitz Purity |
|---|---|---|---|---|---|
| HT 60° C. 0 min | 0.27 | 0.22 | 1.32 | 14.70% | 16.75% |
| HT 60° C. 15 min | 0.26 | 0.22 | 0.77 | 20.74% | 25.28% |
| HT 60° C. 30 min | 0.25 | 0.22 | 0.64 | 22.61% | 28.18% |
| HT 70° C. 15 min | 0.21 | 0.19 | 0.29 | 29.93% | 41.58% |
| HT 70° C. 30 min | 0.21 | 0.20 | 0.13 | 38.18% | 61.49% |
| HT 80° C. 15 min | 0.24 | 0.22 | 0.19 | 36.82% | 55.35% |
| HT 80° C. 30 min | 0.24 | 0.22 | 0.26 | 33.48% | 48.25% |

Table 3 data provide supporting evidence of the use of a product temperature of 70° C. to maximize product purity. Of particular interest is the marked reduction in purity associated with the data taken at 60° C. This can possibly be explained by the incomplete precipitation of the Kunitz impurities below 70° C. Incubation at 70° C. for 30 minutes provided a 1:1 weight ratio of PI2 to Kunitz impurities. Extending the duration of the incubation from between 20 minutes and 60 minutes enhanced purity without adversely affecting yield. However, extending the incubation beyond this period did not bring any additional improvement in the purity of PI2 and began to adversely affect yield.

Experiment 2

PI2 stability has been examined by studying peak shape changes discernable using the HPLC analysis for PI2. The relative stability of a 10% pure, lyophilized PI2 product in a solution containing 0.43 M sodium chloride and 0.64% formic acid at 70°, 80° and 90° C. was studied to assist with the time and temperature optimization of the heat treatment process. The PI2 was found to be unstable for periods of longer than 15 minutes at either 80° C. or 90° C. PI2 was observed to be stable at 70° C. for at least 3 hours.

Freeze dried PI2 of approximately 10% purity in an amount of 16.8 mg was dissolved in 10 ml of 0.43 N sodium chloride/0.64% formic acid. The acid and salt levels used to dissolve the PI2 sample were chosen to mimic the resulting concentration from the optimized extraction of whole Russet Burbank potatoes with 1.0 N sodium chloride and 1.5% formic acid solution. These percentages were based on the observed average moisture content in typically extracted, whole raw potatoes. An aliquot of this solution was dispensed into each of 5 vials and the vials were sealed. The vials were then immersed in a water bath for the prescribed period of time, removed and cooled by immersion in an ice bath.

TABLE 4

PI2 peak area of samples incubated at 90° C.

| Time (minutes) | PI2 Area |
|---|---|
| 0 | 10213 |
| 30 | 10063 |
| 60 | 10000 |
| 120 | 10150 |
| 180 | 10576 |

TABLE 5

PI2 peak area of samples incubated at 80° C.

| Time (min) | PI2 Area |
|---|---|
| 0 | 11254.1 |
|  | 11178.2 |
| 30 | 11486.1 |
|  | 11079.8 |
| 60 | 11298.6 |
|  | 9798.97 |
| 120 | 10028.1 |
|  | 8706.6 |
| 180 | 11482 |
|  | 11409.8 |

TABLE 6

PI2 Stability in samples incubated at 70° C.

| Time (min) | PI2 Area |
|---|---|
| 0 | 9915.1 |
|  | 9323.8 |
| 30 | 10298.5 |
|  | 9887.1 |
| 60 | 10138.1 |
|  | 9786.78 |
| 120 | 10189 |
|  | 9056.65 |
| 180 | 9788.12 |
|  | 9598.64 |

Table 4 data indicate that the total amount of PI2, active and denatured, remains relatively unchanged during the 3 hours of heating at 90° C. However, upon reaching the target temperature (90° C., 0 min) the peak shape produced in the HPLC by PI2 is significantly broadened, supplying evidence of a conformational change. The same situation occurred at 80° C. with peak broadening occurring by the thirty-minute time point (Table 5). The sample was perfectly stable 70° C. with no evidence of denaturation(peak broadening) evident even after 3 hours. The change in the peak shape evident at temperatures above 70° C. dictates the upper temperature limitation at 70° C. (Table 6). One method of pasteurization requires a product temperature of 70° (HTST). The temperature threshold of 70° C. is therefore ideal for dual functionality of protein purification and pasteurization.

Experiment 3

The effects of product chilling were examined in order to maximize protein purity. Samples were taken from the heat treatment trials, at varied temperature points during the cooling stage of the isolation process. These samples were analyzed by HPLC and protein purity was determined. For this study the protein purity value was defined as the amount of PI2 compared to the sum of the PI2 and 'Kunitz' impurities found in each individual sample. The 'Relative protein purity gain' is the percentage gain, normalized to the maximum purity realized.

TABLE 7

Effect of product chilling on protein purity

| Chill final temperature | Raw protein purity gain | Relative protein purity gain |
|---|---|---|
| 70° C. | 0.00% | 0.00% |
| 60° C. | 0.21% | 0.37% |
| 50° C. | 1.09% | 1.92% |
| 40° C. | 1.82% | 3.21% |
| 35° C. | 2.11% | 3.72% |
| 30° C. | 2.89% | 5.09% |
| 25° C. | 3.03% | 5.34% |
| 20° C. | 3.09% | 5.45% |

The product cooling study highlighted the protein purity gained by cooling the heat treatment product. While only small gains are realized above 40° C., the five percent gain in purity achieved by cooling to 25° C. can be critical to the success of the process. A five percent gain in protein purity will translate to a similar boost in final product, protein purity. Additionally, achieving an increased protein-purity, prior to micro and ultrafiltration, will conserve processing time, costs, and membrane lifetimes.

Experiment 4

An experiment was run to evaluate the heat stability of the PI2 product obtained under the present process after extraction, heat treatment to 70° C., clarification, ultrafiltration and lyophilization. The lyophilized PI2 product was dissolved in a solution of 0.75 M NaCl and 0.5% formic acid. This solution was chosen to approximate the composition of the initial extract obtained when using the normal extraction procedure with 426 g of 1.5 N NaCl and 1% formic acid is used to extract 1 kg of potatoes. The lyophilized PI2 was used instead of the initial extract due to the presence of the Bowman-Birk impurities that co-elute with PI2 under the reverse phase HPLC procedure and thereby interfere with quantitation. The PI2 concentration was chosen to approximate the normal concentration of PI2 found in the initial extract. The test solution was prepared and 1 ml was placed in HPLC vials which were sealed and heated in a 90° C. water bath for time periods from 0 minutes to 180 minutes. After cooling, the vials were analyzed for PI2 content via HPLC. The results are given in Table 8.

TABLE 8

PI2 Stability at 90° C.

| Time (minutes) | PI2 mg/ml |
|---|---|
| 0 | 0.188 |
| 30 | 0.186 |
| 60 | 0.181 |
| 120 | 0.180 |
| 180 | 0.189 |

It is clear from Table 8 that the total amount of PI2 is unchanged during the 3 hours of heating at 90° C. The peak shape produced in the HPLC by PI2 wash also unchanged, giving some evidence of retention of activity. It has been observed that under slightly different conditions, that is, 80° C., 0.5% formic acid and 4 N NaCl, that PI2 does precipitate out and that the HPLC peak shape broadens, indication denaturation. This process occurred over a period of 12 hours with the NaCl concentration increasing from 0.6 M to the final value of 4 N.

Filtration Stage

Ultrafiltration of the clarified extract from the PI2 isolation process is an important step in the isolation and purification procedure as multiple goals are accomplished using a comprehensive separation method. Clarified PI2 extract is concentrated, or dewatered, through ultrafiltration. Ultrafiltration also serves to remove low molecular weight impurities, including sugars and proteins. Sodium chloride and formic acid used in the extraction steps are also removed during ultrafiltration. To remove the acid content of the clarified extract, an appropriate buffer system is required. The chemical nature of the buffer must not adversely affect final product composition, while its concentration needs to balance pH change capacity, and membrane compatibility. As low molecular weight impurities are removed through the entire ultrafiltration process, the volume of buffer used in the product dialysis should be minimized for cost effectiveness whereas increasing the number of filtration cycles will improve overall final protein purity.

Experiment 1

A process for the isolation of PI2 from whole potatoes was developed in an attempt to maximize yield, minimize impurities, minimize cost, and achieve commercial feasibility. Ultrafiltration of clarified PI2 extract was examined by monitoring the following variables: membrane composition, nominal molecular weight cut-off, concentration factor, flow rate, diafiltration buffer choice, buffer concentration, and diafiltration solution volume. In a preferred embodiment, the membrane composition is regenerated cellulose, the nominal molecular weight cut-off is 10,000 Dalton, the concentration factor achieved is 10 times original volume, the flow rate is 45 liters/(hour-meter$^2$) (LMH) at a 20 psig retentate pressure using an ammonium bicarbonate ($NH_4HCO_3$) buffer system, the diafiltration buffer is 100 mM, and 6 times the concentrated volume is used as diafiltration feed.

Protease Inhibitor Recovery

Three different filter types were examined, the Pall Filtron Centramate CS010C12, (Pall Corporation, East Hills, N.Y.), the Pall Filtron Maximate CS010G02, and the A/G Technology UFP-5-C-4A, (A/G Technology Corporation, Needham, Mass.). Each filter was tested under a range of conditions consistent with its specifications. All of the filters were found to be non-fouling under the tested conditions, but the Maximate filter had an average flux of 63 liters/(hour-meter$^2$), compared to 54.7 for the Centramate and 20.2 for the A/G Technology filter. Final diafiltered solutions from an A/G Technology trial and from a Pall Filtron trial were freeze dried (lyophilized) and the product analyzed for PI2 content. Protein content is determined according to the Bradford protein assay (Bradford, M. M. A rapid and sensitive method for the quantitation of microgram quantities of protein utilizing the principle of protein-dye binding. *Anal. Biochem.* 72: 248-254, 1976) using the Pierce Coomassie Plus Protein Assay 23236. Five hundred ml of extract was supplied for diafiltration. PI2/kg potato calculation assumed that 100 kg of potatoes yielded 90 kg of extract. A 90 kg extract yield was a standard value for extractions utilizing whole potatoes.

TABLE 9

Relative Protease Recovery

| Filter | Gross crude product (mg) | % PI-2 | Total PI-2 (mg) | PI-2/kg potato (mg) |
|---|---|---|---|---|
| A/G Tech UFP-5-C-4A | 630 | 7.60 | 47.88 | 86.2 |
| Pall Filtron Centramate CS010C12 | 800 | 9.61 | 76.88 | 138.4 |

The A/G Technology membrane retained only 62.3% of the protease inhibitor in comparison to that recovered by the Pall Filtron membrane. Analyses were completed in duplicate and the results reported as an average. A comparison of the respective membranes resulted in a somewhat surprising conclusion. While the A/G Technology membrane is rated at 5,000 NMWCO, and the Pall Filtron membrane is rated at 10,000 NMWCO, there are no industry standards regarding the testing for nominal molecular weight cutoff. Due to differences in the respective pore geometries of the Pall Filtron cellulosic membrane and the A/G Technology polysulfone membrane, passage of protein is not only molecular mass dependent, but also molecular geometry dependent. Further collaborating the relative permeability of the A/G Technology membrane to potato protease inhibitor is the observation that a 10,000 NMWCO filter passes greater than 95% of the protease through the membrane—thus all the tests described above were done using the 5000 NMWCO membrane from A/G Technology. Moving to a 1000 NMWCO membrane resulted in dramatically reduced flux.

Diafiltration Buffer

Diafiltration against water resulted in rapid and irreversible fouling of the membrane with a corresponding flux rate decay. Accordingly, it was necessary to identify a buffer system that would prevent or reduce fouling and be compatible with the concentration step, the composition of the final product, the selected membrane, and the lyophilization step. Following testing, a 100 mM ammonium bicarbonate buffer having a conductivity of 5.22 mS/mol was selected. A 6×volume wash appears to be sufficient for removal of the organic acid and salt, increasing product purity, and results in a neutralized solution.

To prevent fouling and to maintain the membrane, cleaning was performed by flushing with 0.1 N NaOH for 30 minutes with a crossflow of ~600 ml/minute at 7.7 TMP. Membranes cleaned in accordance with this procedure recovered nearly 100% (99.4%) of initial performance characteristics. Typically, a filter loses 15-20% of its initial performance characteristics after a first use, and thereafter attains, with proper maintenance, a performance plateau that provides consistent and repeatable results for an extended period of use.

The use of 100 mM ammonium bicarbonate during the diafiltration phase of PI2 purification prevents fouling of the cellulosic membrane and allows for removal of a major impurity, carboxypeptidase inhibitor, which elute after PI2 in HPLC. When water is used as a diafiltration buffer, irreversible fouling occurs quickly and the impurity is retained.

Integration values demonstrate that the impurity is contained at about one-third of the concentration of PI2. After concentration of the sample on the ultrafilter, during which time some of the low molecular weight impurities co-eluting with PI2 are lost, the ratio of impurity to PI2 is essentially unchanged. Diafiltration against 6 volumes of 100 mM ammonium bicarbonate results in a substantially reduced ratio of impurity to PI2. Diafiltration against larger volumes of ammonium bicarbonate exhibited almost complete removal of the impurity after 20 volumes. The ratio of impurity to PI2 observed when using water as the diafiltration buffer remained unchanged.

TABLE 10

Effect of Diafiltration with 100 mM Ammonium Bicarbonate

| Sample | PI2 Integrated Area (mAU) | Doublet Impurity Integrated Area (mAU) | Ratio Impurity: PI2 |
|---|---|---|---|
| Heat Treated Extract | 2917 | 1119 | 0.384 |
| Concentrated Extract | 17133 | 6574 | 0.384 |
| 6X Diafiltered against AMBI | 25166 | 3767 | 0.150 |
| 10X Diafiltered against AMBI | 13967 | 1135 | 0.081 |
| 20X Diafiltered against AMBI | 17965 | 281 | 0.016 |
| ~5X Diafiltered against Water | 4648 | 1596 | 0.343 |

The use of water as the diafiltration liquid is contraindicated due to the fouling of the filter and the retention of impurities removed using 100 mM ammonium bicarbonate.

CONCLUSIONS

The developed process is highly efficient in the separation and removal of Kunitz and Bowman-Birk proteinase inhibitors. Regular heating and washing conditions result in the recovery of about 160 mg PI2/kg potato at approximately 90% w/w purity in the protein fraction. The process, moreover, can be adjusted to modify the amount of PI2 recovery in favor of purity, and oppositely, to improve yield at a lower purity. The elimination of certain protein impurities is necessary in certain applications. For example the satiety extending effect of PI2 requires that the PI2/Kunitz level be less than 1. This level of reduction in Kunitz impurities can be achieved by following this process through the denaturation and subsequent centrifugation stage without the need to conduct ultrafiltration or diafiltration. According, the Kunitz impurities can be effectively removed by the use of simple and inexpensive equipment, essentially a heating pot and centrifuge.

PI2 in a 1.5% formic acid and 1.0N NaCl solution was shown to be stable when heated to 70° C. for up to one hour, whereas the solubility of the other proteins decreased. Incubation at 70° C. for 30 minutes was sufficient to achieve a 1:1 ratio between PI2 and Kunitz inhibitors. Extending the incubation time from 30 minutes to one hour enhance purity without adversely affecting yield. Extending the incubation period beyond one hour did not bring any additional improvements in the purity of PI2 and began to affect yield. The denaturation of PI2 was more obvious when incubated at 80° C. or greater in the presence of similar acid and salt concentrations. Heating at 80° C. for less than 15 improved the purity of PI2 but adversely affected yield.

The highest PI2 yields were achieved when the incubation is performed at below 70° C., most likely because any heat degradation of PI2 was minimized. However, incubation at temperatures less than 70° C. compromise the purity of PI2 recovered because the Kunitz and Bowman-Birk inhibitors are more stable under these conditions.

The heat treatment stage should be carried out at 80° C. or greater for between 15 minutes and three hours in order to prepare a PI2 product at a purity of 90% w/w or greater. Incubation at between about 70° C. and about 80° C. for periods of approximately one hour are used to prepare a PI2 product of intermediate purity and yield. Incubation at 70° C. or less is used to maximize the yield of PI2 with some sacrifice in purity.

Ultrafiltration optimization required choosing the correct membrane material. The filter material choices were either cellulose or polyethersulfone. It was found that either of these materials was acceptable, with the cellulose being the better choice due to decreased blinding during ultrafiltration and equal ease of cleaning after usage. The molecular weight cutoff for filter selection is either 5,000 Daltons or 10,000 Daltons. Either of these pore sizes was suitable for retaining the PI2, which has a molecular mass of 21,000 Daltons. It was found that no PI2 was lost through the 10,000 Dalton filter and that ultrafiltration rates were approximately twice as fast in comparison to the 5,000 Dalton filter. Total cross flow rates of greater than 7 liters/(hour-meter$^2$) of filter with a back pressure of 20-25 psig afforded the fastest ultrafiltration with no membrane fouling. Cleaning the membrane with a solution of 0.1 N sodium hydroxide, as recommended by the manufacturer, was sufficient to maintain an optimal filtration rate on a laboratory prepratory scale The use of water as a diafiltration buffer was contraindicated due to rapid fouling of the filter. The use of 100 mM ammonium bicarbonate as a diafiltration buffer prevented fouling by presenting an ionic strength sufficient to discourage precipitation of solids onto the filter. Ammonium bicarbonate also promoted the removal of some impurities, and was readily removed via lyophilization.

The results of the studies described herein demonstrate that for reproducibility, maximum yield, impurity removal, minimal cost, and maximum commercial feasibility, the conditions described herein are ideally suited for achieving a desired result. An ideal membrane composition comprises regenerated cellulose utilizing Maximate geometry with a nominal molecular weight cut-off of 10,000 Dalton. A flow rate across the regenerated cellulose membrane of 60 LMH at 0.4 L/minute per membrane square foot is ideal to achieve a concentration factor of 10 times volume of the clarified extract volume when using an ammonium bicarbonate diafiltration buffer at a working concentration of 100 mM diafiltered against six times the concentrated volume.

The foregoing description comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

What is claimed is:

1. A method for adjusting the yield and purity of potato proteinase inhibitor II extracted from raw potato tubers, comprising the steps of:
   (a) extracting the potato proteinase inhibitor II and other protein products from the potato tubers by preparing a mixture of an organic acid selected from the group consisting of acetic, ascorbic, citric and formic acid, and comminuted potato tubers to form a solid fraction and a liquid fraction comprising the potato proteinase inhibitor II and other protein products, wherein said extraction is carried out in the absence of alcohol;
   (b) heating the liquid fraction of part (b) to a temperature between about 60° C. to about 90° C. for a time period between about 30 to about 180 minutes to selectively affect the purity and yield of the potato proteinase inhibitor II; and
   (c) removing denatured protein products to prepare a clarified extract solution.

2. The method of claim 1 wherein the mixture of part (a) comprises formic acid and sodium chloride.

3. The method of claim 1 wherein the mixture of part (a) comprises about 0.5% to about 2.5% of formic acid and 0 to 3.0 N of sodium chloride.

4. The method of claim 1 wherein the time period of part (b) is between 15 and 60 minutes.

5. The method of claim 1 wherein the step of removing the denatured proteins is carried out by centrifugation.

6. The method of claim 1, further comprising filtering the clarified extract to remove impurities having a molecular weight below that of the potato proteinase inhibitor II.

7. The method of claim 6 wherein filtration is conducted on an ultrafiltration membrane having a molecular weight cut-off rating of about 5 KD to about 10 KD.

8. The method of claim 6 wherein a buffer solution comprising an aqueous solution of ammonium bicarbonate is added during filtration.

9. The method of claim 8 wherein the buffer is between about 50 and about 500 mM ammonium bicarbonate.

10. The method of claim 6 wherein the clarified extract is concentrated to less than one-fifth of the starting volume during filtration.

11. The method of claim 10 wherein the filtration step further comprises washing the clarified extract with up to ten volumes of filtration buffer.

\* \* \* \* \*